United States Patent
Geddes (10) Patent No.: US 9,310,303 B2
(45) Date of Patent: Apr. 12, 2016

(54) VOLTAGE GATED METAL-ENHANCED FLUORESCENCE, CHEMILUMINESCENCE OR BIOLUMINESCENCE METHODS AND SYSTEMS

(71) Applicant: UNIVERSITY OF MARYLAND, BALTIMORE COUNTY, Baltimore, MD (US)

(72) Inventor: Chris D. Geddes, Bel-Air, MD (US)

(73) Assignee: UNIVERSITY OF MARYLAND, BALTIMORE COUNTY, Baltimore, MD (US)

(*) Notice: Subject to any disclaimer, the term of this patent is extended or adjusted under 35 U.S.C. 154(b) by 27 days.

(21) Appl. No.: 14/223,254

(22) Filed: Mar. 24, 2014

(65) Prior Publication Data

US 2014/0206075 A1    Jul. 24, 2014

Related U.S. Application Data

(62) Division of application No. 12/920,937, filed as application No. PCT/US2009/035620 on Mar. 1, 2009, now Pat. No. 8,679,855.

(60) Provisional application No. 61/033,231, filed on Mar. 3, 2008.

(51) Int. Cl.
   *G01N 21/64*     (2006.01)
   *G01N 33/543*    (2006.01)

(52) U.S. Cl.
   CPC ........ *G01N 21/648* (2013.01); *G01N 33/54373* (2013.01)

(58) Field of Classification Search
   CPC .................. G01N 21/648; G01N 33/54373
   See application file for complete search history.

(56) References Cited

U.S. PATENT DOCUMENTS

| | | |
|---|---|---|
| 5,017,009 A | 5/1991 | Schutt et al. |
| 5,449,918 A | 9/1995 | Krull et al. |
| 5,866,433 A | 2/1999 | Schalkhammer et al. |
| 5,926,284 A | 7/1999 | Naya et al. |

(Continued)

FOREIGN PATENT DOCUMENTS

| | | |
|---|---|---|
| EP | 1239279 | 9/2002 |
| JP | 2006-177725 | 7/2006 |

(Continued)

OTHER PUBLICATIONS

Aslan, K. et al. Microwave-accelerated metal-enhanced fluorescence: Platform technology for ultrafast and ultrabright assays, Analytical Chemistry 2005, 77, 8057-8067.

(Continued)

*Primary Examiner* — Melanie Y Brown
(74) *Attorney, Agent, or Firm* — Marianne Fuierer; Moore & Van Allen, PLLC (57) ABSTRACT

In the present invention, it is demonstrated for the first time, the influence of electrical current on the ability of surface plasmons to amplify fluorescence signatures. An applied direct current across silver island films (SiFs) of low electrical resistance perturbs the fluorescence enhancement of close-proximity fluorophores. For a given applied current, surface plasmons in "just-continuous" low resistance films are sparsely available for fluorophore dipole coupling and hence the enhanced fluorescence is gated as a function of the applied current.

5 Claims, 8 Drawing Sheets

(56) References Cited

U.S. PATENT DOCUMENTS

| | | |
|---|---|---|
| 7,095,502 B2 | 8/2006 | Lakowicz et al. |
| 7,253,452 B2 | 8/2007 | Steckel et al. |
| 7,267,948 B2 | 9/2007 | Vo-Dinh |
| 7,348,182 B2 | 3/2008 | Martin et al. |
| 7,351,590 B2 | 4/2008 | Martin |
| 7,384,792 B1 | 6/2008 | Wang et al. |
| 7,400,397 B2 | 7/2008 | Lakowicz et al. |
| 7,648,834 B2 | 1/2010 | Moore |
| 7,718,445 B2 | 5/2010 | Martin |
| 7,718,804 B2 | 5/2010 | Geddes et al. |
| 7,732,215 B2 | 6/2010 | Geddes et al. |
| 7,939,333 B2 | 5/2011 | Geddes et al. |
| 8,008,067 B2 | 8/2011 | Geddes et al. |
| 8,034,633 B2 | 10/2011 | Geddes |
| 8,075,956 B2 | 12/2011 | Geddes et al. |
| 2002/0061591 A1 | 5/2002 | Choong et al. |
| 2002/0160522 A1 | 10/2002 | Rubinstein et al. |
| 2003/0228682 A1 | 12/2003 | Lakowicz et al. |
| 2004/0157237 A1 | 8/2004 | Malak et al. |
| 2005/0053974 A1 | 3/2005 | Lakowicz et al. |
| 2006/0011862 A1 | 1/2006 | Bernstein |
| 2006/0147927 A1 | 7/2006 | Geddes et al. |
| 2007/0269826 A1 | 11/2007 | Geddes et al. |
| 2008/0215122 A1 | 9/2008 | Geddes et al. |
| 2009/0022766 A1 | 1/2009 | Geddes et al. |
| 2009/0325199 A1 | 12/2009 | Geddes et al. |
| 2010/0062545 A1 | 3/2010 | Geddes et al. |
| 2010/0209937 A1 | 8/2010 | Geddes et al. |
| 2010/0297016 A1 | 11/2010 | Geddes et al. |
| 2011/0020946 A1 | 1/2011 | Geddes |

FOREIGN PATENT DOCUMENTS

| | | |
|---|---|---|
| WO | WO89/09408 | 10/1989 |
| WO | WO2004/024191 | 3/2004 |
| WO | WO2006052548 | 5/2006 |
| WO | WO2006/074130 | 7/2006 |

OTHER PUBLICATIONS

Aslan, K. et al. Metal-enhanced fluorescence: an emerging tool in biotechnology, Current Opinion in Biotechnology 16, 55-62 (2005).

Aslan, K. et al. Angular-dependent metal-enhanced fluorescence from silver colloid-deposited films: opportunity for angular-ratiometric surface assays, Analyst 132, 1112-1121 (2007).

Aslan, K.; Zhang, Y.; Hibbs, S.; Baillie, L.; Previte, M. J.; Geddes, C. D., Microwave-accelerated metal-enhanced fluorescence: application to detection of genomic and exosporium anthrax DNA in < 30 seconds, Analyst 2007,132, 1130-8.

Aslan, K. et al. Microwave-accelerated and metal-enhanced fluorescence myoglobin detection on silvered surfaces: Potential application to myocardial infarction diagnosis, Plasmonics, 2006, 1, 53-59.

Aslan, K. et al. Microwave-Accelerated Ultrafast Nanoparticle Aggregation Assays Using Gold Colloids, *Anal Chem*, 2007, 79, 2131-6.

Bauer, G. et al. Metal Nano-Cluster Biosensors, Mikrochim. Acta 131, 107-114 (1999).

Boehm, D. A. et al. On-chipe Microfluidic Biosensor for Bacterial Detection and Identification, Sensors and Actuators B—Chemical 2007,126, 508-514.

Cannone, F. et al. Voltage Regulation of Fluorescence Emission of Single Dyes to Gold Nanoparticles. Nano Letters, 2007, vol. 7, No. 4, 1070-1075.

Chowdhury, M. H. et al. Metal-enhanced chemiluminescence: Radiating plasmons generated from chemically induced electronic excited states, Applied Physics Letters, 2006, 88, 173 104.

Geddes, C. et al. Metal-enhanced fluorescence, Journal of Fluorescence 12, 121-129 (2002).

Lacowicz, R. et al. Radiative decay engineering: 2. Effects of silver island films on fluorescence intensity, lifetimes, and resonance energy transfer, Analytical Biochemistry, 2002, 301, pp. 261-277.

Leveque-Fort, S. et al. Nanostructured thin films for fluorescence enhancement. Plasmonics in Biology and Medicine, Proceedings of SPIE, 2004, vol. 5327, pp. 29-36.

Liu. H.W. et al. Bias dependence of tunneling-electron-induced molecular fluorescence from porphyrin films on noble-metal substrates, Physical Review B, 2007, 75.

Makinen, A. J. et al. STM-Induced Light Emission from Substrate-Tethered Quantum Dots, Journal of Physical Chemistry C, 2007,111, 8188-8194.

Schalkhammer, T. Metal Nano Clusters as Transducers for Bioaffinity Interactions, Monatschefte für Chemie 129, 1067-1092 (1998).

Zhang, Y. et al. Low Temperature Metal-Enhance Fluorescence, J Fluoresc 2007, 17, 627-631.

Zhang, Y. et al. Voltage-Gated Metal-Enhanced Fluorescence. J Fluoresc 2009, 19, No. 14, pp. 363-367.

Cannone, F. et al. Supporting Information: Voltage Regulation of Fluorescence Emission of Single Dyes Bound to Gold Nanoparticles. Nano Letters, Mar. 9, 2007, pp. 1-5.

Canadian Office Action, corresponding to Canadian Patent Application No. 2,723,391, issued by the Canadian Intellectual Property Office, on Jul. 8, 2015.

VOLTAGE GATED METAL-ENHANCED FLUORESCENCE, CHEMILUMINESCENCE OR BIOLUMINESCENCE METHODS AND SYSTEMS

CROSS-REFERENCE TO RELATED APPLICATIONS

This application is a divisional application of U.S. patent application Ser. No. 12/920,937, filed on Dec. 2, 2010, now U.S. Pat. No. 8,679,855, which in turn was filed under the provisions of 35 U.S.C. §371 and claimed the priority of International Patent Application No. PCT/US2009/035620 filed on Mar. 1, 2009, which in turn claimed priority of U.S. Provisional Application No. 61/033,231 filed on Mar. 3, 2008, the contents of all applications are incorporated by reference herein for all purposes.

BACKGROUND OF THE INVENTION

1. Technical Filed

The present invention relates generally to Metal Enhanced Fluorescence (MEF), and more particularly, the ability to manipulate the MEF emission by turning "on and off" the emission by passage of direct current through metallic interconnected particles of low electrical resistance.

2. Related Art

Figure 4:
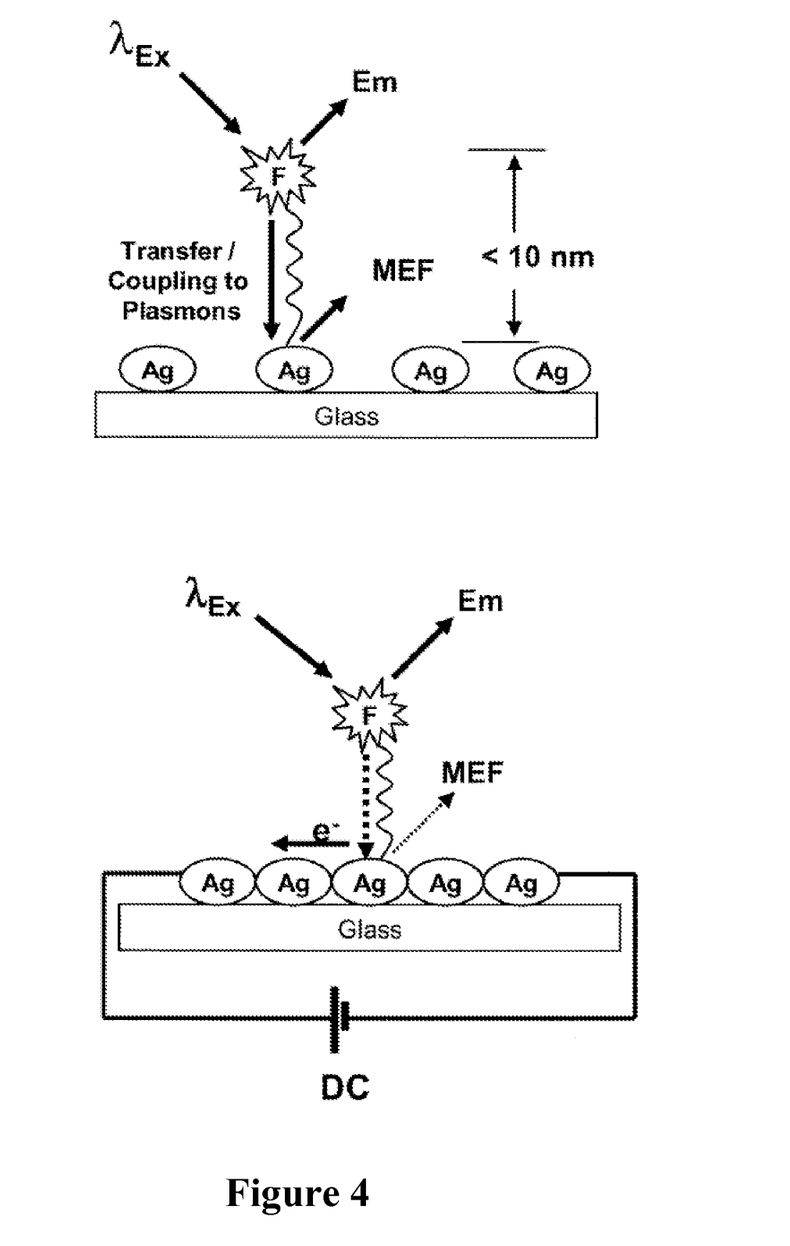
FIG. 4 shows a graphical representation of the current interpretation of Metal-Enhanced Fluorescence (Top), Metal-Enhanced Fluorescence perturbed with applied Voltage/Current (Bottom). F—Fluorophore, MEF—Metal-Enhanced Fluorescence, Ag—Silver nanoparticles.

For many years the effects of fluorophores near-to plasmon resonant particles has been reported, with a perspective of both developing a fundamental understanding of the Metal-Enhanced Fluorescence (MEF)[1-3] phenomenon and secondly, applying the enhanced photophysical properties of fluorophores to biological applications.[4] In all of these reports, surface plasmons are induced in the near-field by close proximity fluorophore dipoles, the surface plasmons in turn radiating the coupled quanta, resulting in fluorescence amplification, as shown in FIG. 4—Top. The coupled fluorescence is for the most part very similar to the free-space fluorescence, observed in the absence of the metal, with the exceptions that the radiative lifetime is significantly shorter, which is thought to be underpinned by the plasmon decay[1-3] and the angular-dependent emission of the coupled emission.[5]

Given the intense research currently being undertaken on metal-fluorophore interactions and their applications in biology and clinical diagnostics, it would be advantageous to find other applicable uses of MEF such as being able to turn the MEF on or off (on demand) and useful for technologies such as a lab-on-a-chip and photon detectors.

SUMMARY OF THE INVENTION

The present invention relates to the ability to manipulate MEF emissions by turning "on and off" the emissions with the introduction and passage of a direct current through a metallic "just continuous" film having low electrical resistance.

In one aspect, the present invention relates to a method for manipulating the emissions from a metal enhanced fluorescence system, the method comprising:
a) providing a conductive metal surface on a substrate, wherein the conductive metal surface comprises a just-continuous film on the substrate and wherein the substrate includes glass, quartz, copper or a polymeric material;
b) positioning a molecule near the conductive metallic surface, wherein the molecule is capable of emitting detectable electromagnetic energy and wherein the molecule is positioned a distance from the conductive metallic surface to enhance the intensity of the emitting detectable electromagnetic energy;
c) applying electromagnetic energy in a wavelength sufficient to excite the molecule and cause detectable electromagnetic energy emissions; and
d) connecting the conductive metal surface with a voltage source, such as a battery, solar panel, hydrogen fuel cell, or wind source, and an actuatable switch, wherein opening of the switch allows transference of direct current through the conductive metal surface which reduces or stops detectable electromagnetic energy emissions and closing of the switch provides for detectable electromagnetic energy emissions detectable electromagnetic energy emissions.

The method described above may be used in multiple fluorescence detecting systems, including but not limited to, Microwave Accelerated Metal-Enhanced Fluorescence (MA-MEF), Microwave Triggered Metal Enhanced Chemiluminescence (MT MEC) or Microwave Accelerated Surface Enhanced Raman Scattering (MASERS). The method described above may be used in multiple fluorescence detecting systems, including but not limited to, Microwave Accelerated Metal-Enhanced Fluorescence (MAMEF) and Microwave Accelerated Surface Enhanced Raman Scattering (MASERS). Further, the system may be used in many different assays, including but not limited to, immunoassays, hybridization assays, resonance energy transfer assays, polarization/anisotropy based assays, bioluminescence based assays, chemiluminescence based assays, luminescence based assays, or enzyme-linked immunosorbent assays.

In one embodiment, the molecule comprises a fluorescing component that has the ability to fluoresce when contacted with radiation in the range from UV or IR. Preferably, the fluorescing component is a molecule that does not interfere with any chemical reaction in the assay system.

Preferably, the conductive metallic surface takes the form of a "just continuous" surface which is different from a continuous conductive surface and a non-continuous surface in light of the fact that the "just continuous" surface there is a connecting web of metallic material or particles that include but is not limited to nanostructures, islands, porous metallic matrix, colloids or thin metallic films having a thickness of from about 12 to 17 nm and that have been annealed to provide a cracked film with particle nature. The metallic material may include any form of conductive metal include silver, gold, platinum, aluminum, rhodium and copper, and more preferably the metallic material is silver or copper.

The molecule that is capable of emitting detectable electromagnetic energy includes, but is not limited to fluorophores, chromophores, or luminophores. A compound capable of fluorescing may be an intrinsic fluorophore or a compound attached to an extrinsic fluorophore.

In another aspect, the present invention relates to device system for use is an assay, the system comprising:
a) a conductive metal surface on a substrate, wherein the conductive metal surface is almost continuous on the substrate and exhibiting a low resistance and wherein the substrate includes glass, quartz, or a polymeric material;
b) a molecule positioned on or near the conductive metallic surface, wherein the molecule is capable of emitting electromagnetic energy upon excitation;
c) a source of electromagnetic energy to excite the molecule and cause the emission of electromagnetic energy;
d) a source of direct current attached to the conductive metal surface with the ability to be turned on and off, wherein the direct current is generated by a battery, solar panel, hydrogen fuel cell, or wind source; and e) a detector for measuring emitting electromagnetic energy and/or a detector for measuring direct current through the conductive metal surface.

In yet another aspect, the present invention relates to a method and system that provides for switching a fluorescent signal between the on or off mode that can be used in a detection device, wherein the change in intensity is quantitative and relative to amount of emitting molecules.

Other aspects and advantages of the invention will be more fully apparent from the ensuing disclosure and appended claims.

DETAILED DESCRIPTION OF THE INVENTION

In the present invention, it is demonstrated for the first time, the influence of electrical current on the ability of surface plasmons to amplify fluorescence signatures, i.e. on Metal-Enhanced Fluorescence (MEF). An applied direct current across silver island films (SiFs) of low electrical resistance perturbs the fluorescence enhancement of close-proximity fluorophores. For a given applied current, surface plasmons in "just-continuous" low resistance films are sparsely available for fluorophore dipole coupling and hence the enhanced fluorescence is gated as a function of the applied current. For thicker, low resistance films, sufficient charge carriers are now present in the metal that the MEF is perturbed to a lesser extent, induced surface plasmons readily formed on the surface by the close-proximity dipole.

The meaning of the term "just continuous film" as used herein means a conductive metallic film having a resistance ranging from about 2 to 200 ohms and more preferably, from about 5 to about 60 ohms and most preferably from about 7 to 25 Ohms wherein a direct current communicatively connected to the conductive metallic film cause a reduction in the electromagnetic emission intensity emitted by adjacent fluorophore, chromophore, or luminophore relative to the film wherein the direct current is not connected.

The methods and systems of the present invention may be used in numerous systems and methods including those described in U.S. patent application Ser. No. 10/536,502 entitled HIGH-SENSITIVITY ASSAYS FOR PATHOGEN DETECTION USING METAL ENHANCED FLUORESCENCE; U.S. patent application Ser. No. 11/917,804 entitled METAL-ENHANCED FLUORESCENCE-BASED SENSING METHODS; U.S. patent application Ser. No. 11/718,560 entitled METAL-ENHANCED FLUORESCENCE FROM PLASTIC SUBSTRATES; U.S. patent application Ser. No. 11/719,731 entitled MICROWAVE ACCELERATED ASSAYS; U.S. patent application Ser. No. 11/695,397 entitled MICROWAVE ACCELERATED PLASMONICS; International Patent Application No. PCT/US08/65801 entitled FLUORESCENCE MICROWAVE MICROSCOPY; U.S. patent application Ser. No. 12/036,402 entitled MICROWAVE FOCUSED CHEMILUMINESCENCE; U.S. patent application Ser. No. 11/750,119 entitled ANGULAR DEPENDENT METAL-ENHANCED FLUORESCENCE; U.S. patent application Ser. No. 12/020,571 entitled METAL-ENHANCED SINGLET OXYGEN GENERATION; U.S. patent application Ser. No. 11/917,075 entitled BIOASSAYS USING PLASMONIC SCATTERING FROM NOBLE METAL NANOSTRUCTURES; and U.S. patent application Ser. No. 11/997,778 entitled NANOSTRUCTURES FOR POLARIZED IMAGING AND RECEPTOR/LIGAND QUANTIZATION, the contents of such applications are hereby incorporated by reference herein for all purposes.

It is known that conducting metallic surfaces can respond to a fluorophores oscillating dipole and modify the rate of emission, which is the intrinsic radiative decay rate, and the spatial distribution of the emitted radiation. Theoreticians describe this effect as due to changes in the photonic mode density near the fluorophore. In most spectroscopic measurements, the solution or medium is transparent to both the emitted and sampling radiation. However, there are several important exceptions to the free space condition. One well-known example is Surface Enhanced Raman Scattering (SERS). It is known that the presence of a metallic surface can enhance the Raman signals by factors of $10^3$ to $10^8$, and reports of even larger $10^{14}$-$10^{16}$ fold enhancements have appeared. The presence of a nearby metal film, island or particle can also alter the emission properties of fluorophores. The most well known effect is the quenching of fluorescence by a near-by metal. The emission of fluorophores within 50 Å of a metal surface is almost completely quenched. This effect is used in fluorescence microscopy with evanescent wave excitation. The emission from membranes cellular regions near the quartz-water interface is quenched, allowing selective observation of the emission from the cytoplasmic region more distance from the solid-liquid interface. In addition to quenching, it is known that metal surfaces or particles can cause significant increases in fluorescence. Remarkably, depending on the distance and geometry, metal surfaces or particles can result in enhancement factors of many 1000 fold for the fluorescence emission of fluorophores.

"Fluorophore," and "fluorescence label," used interchangeably herein, means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™. sulfonyl chloride, BODIPY™, naphthalamine sulfonic acids including but not limited to 1-anilinonaphthalene-8-sulfonic acid (ANS) and 6-(p-toluidinyl)naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2 [(di-n-butylamino)-6 naphthyl]vinyl]pyridinium betaine (Naphtyl Styryl), 3,3'dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1, 4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrimidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

Examples of suitable chemiluminescence labels include but without limitation, peroxidase, bacterial luciferase, firefly luciferase, functionalized iron-porphyrin derivatives, luminal, isoluminol, acridinium esters, sulfonamide and others. A recent chemiluminescent label includes xanthine oxidase with hypoxanthine as substrate. The triggering agent contains perborate, an Fe-EDTA complex and luminol. Choice of the particular chemiluminescence labels depends upon several factors which include the cost of preparing labeled members, the method to be used for covalent coupling to the detector molecule, and the size of the detector molecules and/or chemiluminescence label. Correspondingly, the choice of chemiluminescence triggering agent will depend upon the particular chemiluminescence label being used.

Preferably, the components of the bioluminescence generating system are a luciferase and a luciferin. The bioluminescence generating system may be selected from the group consisting of those isolated from the ctenophores, coelenterases, mollusca, fish, ostracods, insects, bacteria, a crustacea, annelids, and earthworms. The luciferase may be selected from the group consisting of Aequorea, Vargula, Renilla, Obelin, Porichthys, Odontosyllis, Aristostomias, Pachystomias, firefly, and bacterial systems.

Metal-enhanced fluorescence provides enhanced intensity, while simultaneously shortening the lifetime of emissions. The emission enhancement may be observed at distances according to the type of fluorophore to be detected and the type, shape of the metal material, noting a difference between a film and a metallic island or colloid. For example, emission enhancement may be observed when a fluorophore is positioned a distance about 7 nm to about 40 nm to metal surfaces. Preferable distances are about 7 nm to about 30 nm, and more preferably, 10 nm to about 20 nm to metal surfaces.

Fluorescence can be detected using devices including, but not limited to, a spectrofluorometer having a light source and detector. Additional detectors may include GaAs-cathode PMT. Further detectors may include photomultiplier tubes. Additionally, it is advantageous for the device to have a monochromator so that specific wavelengths of light may be used to excite a molecule or to detect emissions at a specific wavelength.

Excitation light sources can include arc lamps and lasers, laser diodes and light emitting diode source, and both single and multiple photon excitation sources. In another embodiment, use of a Ti-sapphire laser, Laser Diode (LD) or Light Emitting Diode Sources (LEDs) may be used with the RNA assay of the present invention. For example, using 2-photon excitation at 700-1000 nm and also using short pulse width (<50 pi), high repetition rate (1-80 MHz), laser diode and LED (1 ns, 1-10 MHz) sources. The enhanced sensitivity of the assay using 2-photon excitation, as compared to 1-photon, can be shown by using series dilution with RNA, initially with the Ti-Sapphire system, and later with LEDs and LDs. If a fluorophore absorbs two photons simultaneously, it will absorb enough energy to be raised to an excited state. The fluorophore will then emit a single photon with a wavelength that depends on the fluorophore used and typically in the visible spectra. The use of the Ti-sapphire laser with infrared light has an added benefit, that being, longer wavelengths are scattered less, which is a benefit to high-resolution imaging. Importantly, there is reduced background signal level gained by using 2-photon excitation as compared to 1-photon excitation by utilizing localized excitation near by a metallic particles.

When a sample containing a fluorophore, chromophore or luminophore is exposed to an amount of exciting radiation or a involved in a light emitting chemical reaction, the fluorophore, chromophore or luminophore emits radiation that is detectable. The intensity of emissions can be increased in response to an amount of exciting radiation when the distance between the metal particle and the fluorophore, chromophore or luminophore is from about 5 nm to about 200 nm. The enhancement of intensity of emissions is in part due to the localized excitation of the fluorophores when in close proximity to the metallic surface and results in improved photostability of the emitting molecules. Further, the interactions and coupling with the plasmons on the surface of the metallic material provides for additional enhancement.

In one embodiment the metallic particle may be prepared by reduction of metal ions using various reducing agents. For example, sodium hydroxide may be added to a rapidly stirred silver nitrate solution forming a brown precipitate. Then ammonium hydroxide is added to re-dissolve the precipitate. The solution is cooled and dried quartz slides are added to the beaker, followed by glucose. After stirring for 2 minutes, the mixture is warmed to 30° C. After 10-15 minutes, the mixture turns yellow-green and becomes cloudy. A thin film of silver particles is formed on the slides and can be seen from their brown green color. Notably, the length of time the slide remains in the mixture provides for different thicknesses of films. For example if the deposition process is conducted for about 5 to 10 minutes, the deposited films will be considered to be "just continuous." Preferred metals are silver and gold. Again, gold may be used because of the absorption of gold at shorter wavelengths.

Silver island films can also be formed by a chemical reduction of a silver salt on the quartz surface, which are relatively simple to fabricate.

Metallic materials in an amount to form a just continuous film can be bound to a surface by placing functional chemical groups such as cyanide (CN), amine ($NH_2$) or thiol (SH), on a glass or polymer substrate.

Positioning of the biomolecule or metal particle at a desired distance can be achieved by using a film. The film may be a polymer film, a Langmuir-Blodgett film or an oxide film.

Further a metallic film can be prepared by Vacuum Vapor Deposition. The substrate can be pretreated by air plasma under $1\times10^{-4}$ mbar for 3 min before depositing the metal film. A silver wire can be melted on a filament, evaporated under a pressure of $<1\times10^{-7}$ mbar, and deposited onto the glass slides. The deposition rate can be adjusted by the filament current (1 angstrom/sec), and the thickness of film can be measured with a quartz crystal microbalance positioned close-to the glass substrate within the deposition chamber. Preferably, the thickness of the film is between about 12 and 17 nm which can then be annealed for about an hour at about at 200° C. The annealing process is conducted in the absence of oxygen and oxygen can be eliminated by alternately purging the system with ultra-high purity nitrogen (Airgas, MD) and pumping down to vacuum before the annealing process commenced.

Methods and Material

Preparation of Silver Island Films (SiFs) with Different Resistances.

SiFs were prepared as was previously published.[4] In a typical SiFs preparation, a solution of silver nitrate (0.5 g in 60 ml of deionized water) was prepared in a clean 100-mL glass beaker. 200 uL of freshly prepared 5% (w/v) sodium hydroxide solution and 2 ml of ammonium hydroxide were added to a continuously stirred silver nitrate solution at room temperature. The solution was subsequently cooled to 5° C. by placing the beaker in an ice bath, followed by soaking the Silane-Prep™ glass slides in the solution and adding a fresh solution of D-glucose (0.72 g in 15 ml of water). The temperature of the mixture was then warmed to 30° C. As the color of the mixture turned from yellow green to yellowish brown, the beaker was removed from heat and the slides were kept in solution for 5-30 mins depending on the required resistance. The slides were then removed from the mixture, washed with water, dried under $N_2$ and the slides resistance measured with a GDT-11 voltmeter (GB Instruments™).

Preparation of Dried Samples on the Surface.

300 uL FITC (2.5 mM) in ethanol solution was dropped on the surfaces of SiFs, which had different resistances. The solvent was evaporated and the samples were studied. For oxidation and dipole re-orientation studies (control samples), 100 uL FITC was dropped in 1 mL 0.25% (w/v) PVA in water, and spin-coated on the SiFs ($\approx$7 ohm). This procedure produced $\approx$37 nm thick films (measured using AFM) which prevented both the diffusion of oxygen and fluorophore dipoles to reorientate during current flow.

Absorption and Fluorescence Measurements. Absorbance spectra were recorded on a Varian Cary 50 UV-Vis Spectrophotometer. Fluorescence measurements were collected at an angle of 90 degrees to the surface, with 473 nm excitation light incident at 45 degrees to the glass/silvered surface, using a Fiber Optic Spectrometer (HD2000) from Ocean Optics, Inc. Voltage-Gating Experiments. Direct current (Extech Instruments 382213) was applied to the SiFs with different resistances, FIG. 1 Bottom insert, and gated "on and off" during fluorescence measurements.

SEM Measurements.

Scanning electronic microscopy (SEM) was performed on a Hitachi SU-70 instrument. Samples were cut and mounted on an Aluminum support. High voltage, 20 kV, was employed and the samples were investigated at a magnification of 14994×.

Results and Discussion

Interestingly, non-continuous films with a high resistance show no effect with direct current, and thick continuous films with a low resistance, are simply not suitable for plasmon coupling as previously shown.[6] Subsequently, the findings set forth herein suggest that just-continuous films with a low electrical resistance can be used to gate MEF "on and off" and indeed at "in between" emission intensities. Given the recent interest in the uses of MEF, these findings will be of very high significance for lab-on-a-chip based technologies, and in the development of new fluorescence detectors, which directly measure coupled quanta/fluorescence.[7]

Figure 5:
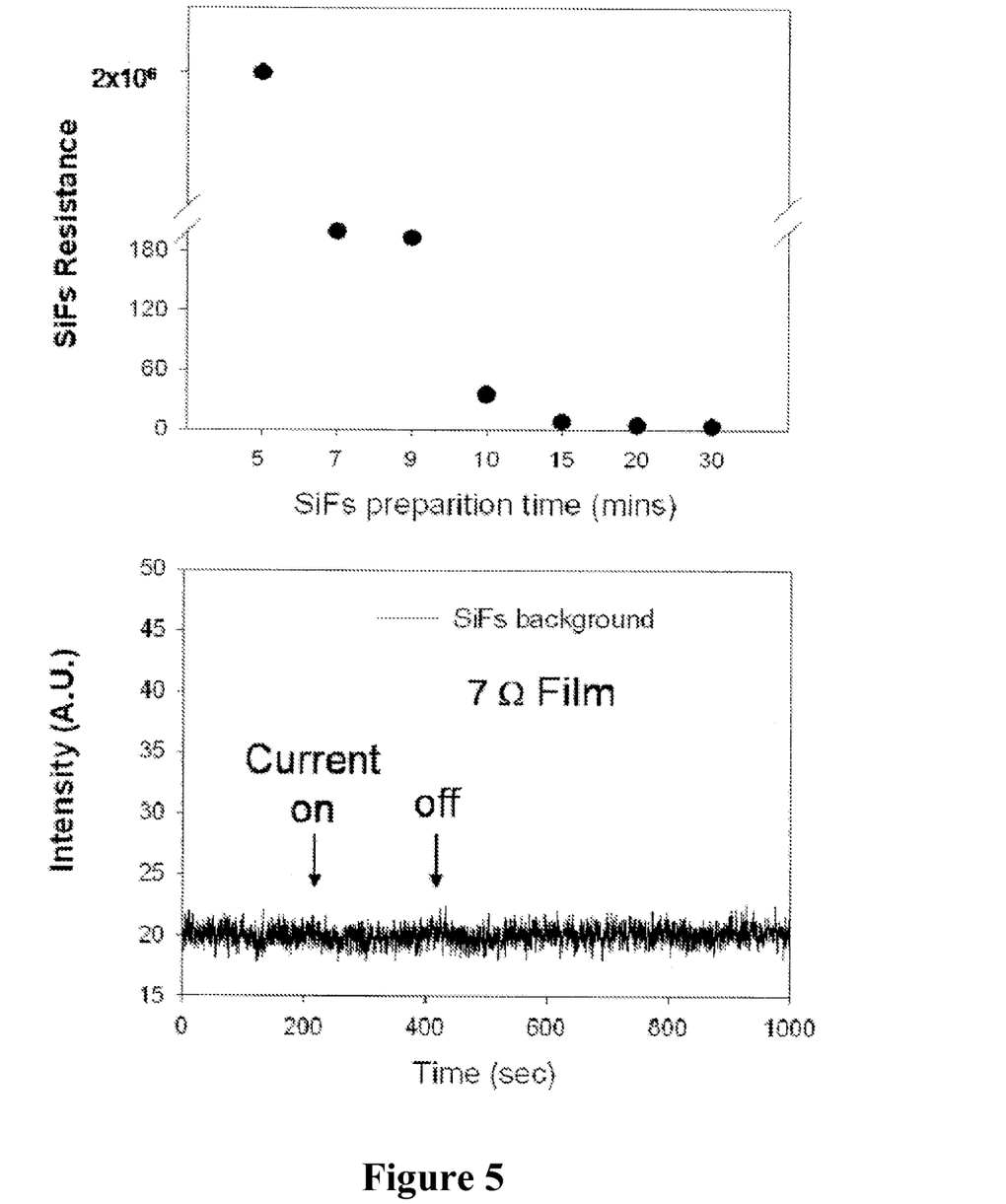
FIG. 5 shows a graph of average SiFs resistance versus different SiFs preparation time (Top). Time dependent background emission from SiFs (measured at 544 nm) for an almost-continuous, ≈7Ω film, with the Voltage/Current gated "on" and "off" (Bottom).

SiFs, which have previously been used for MEF,[4, 8] were deposited on amine-coated glass slides (Sigma), the procedure modified to allow the deposition of SiFs over a longer time-period to modify the electrical resistance of the surfaces, as shown in FIG. 5—Top. Specifically, films deposited for >15 mins were found to be completely conducting (Resistance<1Ω), while films deposited for <5 mins were non-conducting, (Resistance>$10^6$Ω). Films deposited, between about 5-13 mins were "just" conductive, the films having resistances up to several hundred ohms. Scanning Electron Microscope (SEM) images of the surfaces show the particulate (high resistance) to continuous (low resistance) nature of the films, FIGS. 1 and 2 inserts.

Figure 1:
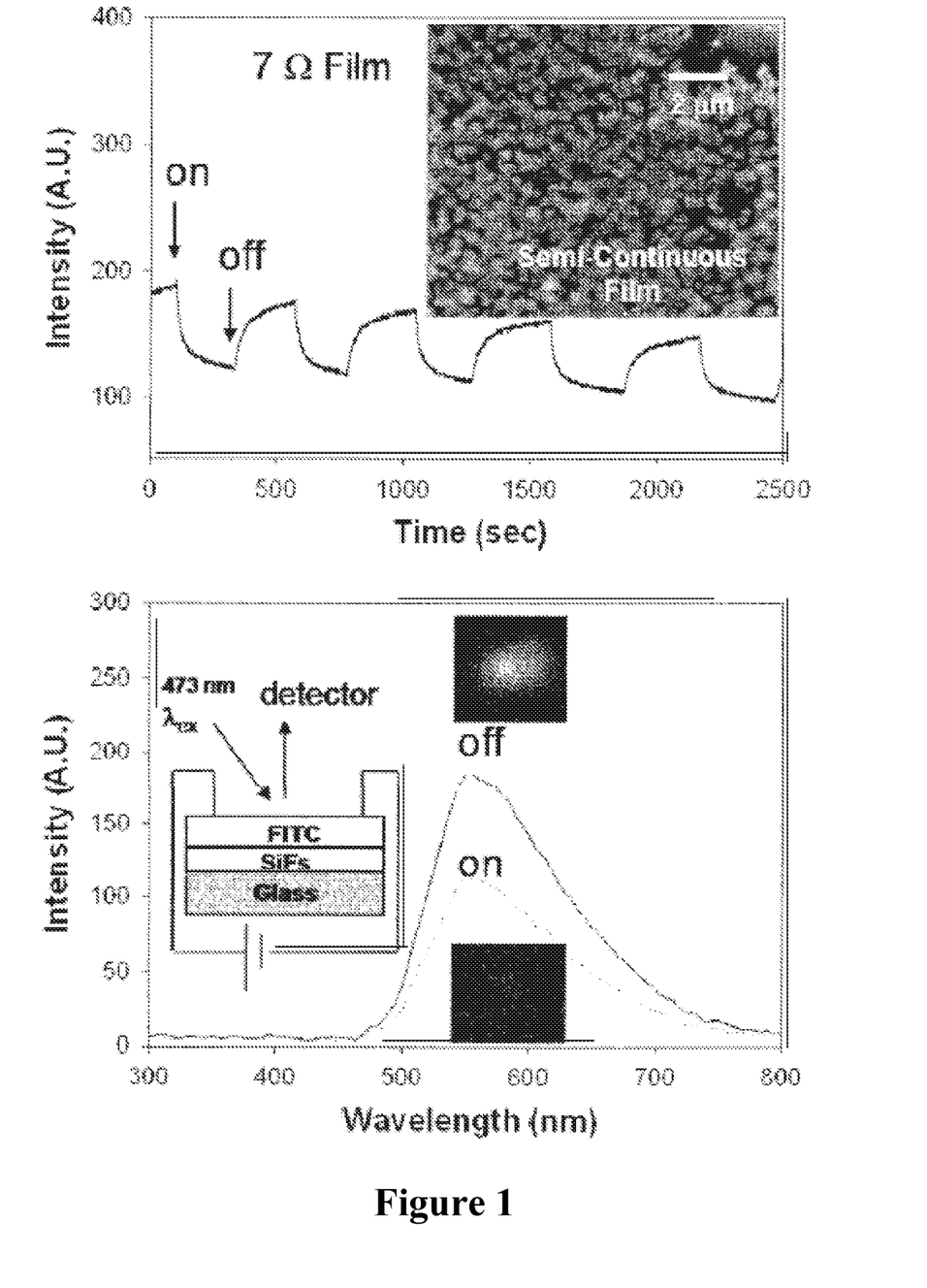
FIG. 1 shows the time-dependent fluorescence emission of FITC (measured at 544 nm) on semi-continuous SiFs with applied "on" and "off voltage (2.1 V, 0.3 A)(Top). Top-insert shows the SEM image of the semi-continuous SiFs film. Bottom—Fluorescence spectra of FITC on SiFs with 2.1 V, 0.3 A, gated on and off. Bottom—inserts show the schematic representation of the experimental set-up and photographs taken through a 473 nm notch filter.

FIG. 1 shows the effects of an applied voltage on fluorescein (FITC) coated on a semi-continuous (just continuous) film (7Ω), the experimental set-up shown in FIG. 1—Bottom-Insert. Remarkably, as the voltage is gated, the FITC fluorescence can be seen to both rise and fall respectively. The fluorescence emission spectra are otherwise spectrally identical during gating, only the magnitude of the intensity fluctuating. The photographs of FIG. 1—Bottom-Insert, show the actual fluorescence during gating.

Figure 6:
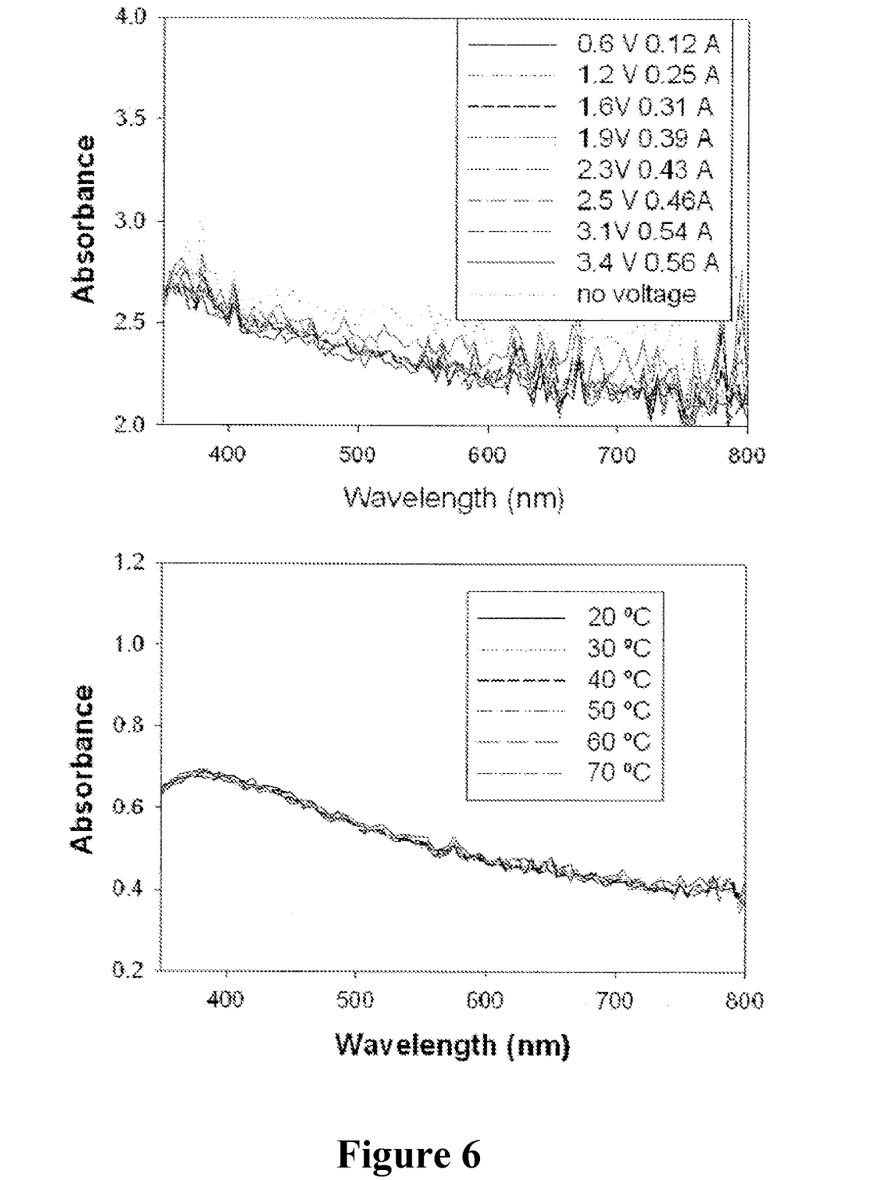
FIG. 6 shows absorption spectra of SiFs as a function of applied voltage/Current (Top). Absorbance spectra of SiFs heated to different temperatures (Bottom).

In a series of detailed control experiments silver background emission (FIG. 5, bottom) and changes in the plasmon absorption as a function of applied current/voltage, as shown in FIG. 6, were eliminated as the possible cause of the effect. Interestingly, as the voltage and current were progressively changed, the FITC emission was subsequently gated respectively (FIG. 7, Top), giving a strong indication that the observations were a result of the applied direct current.

Figure 7:
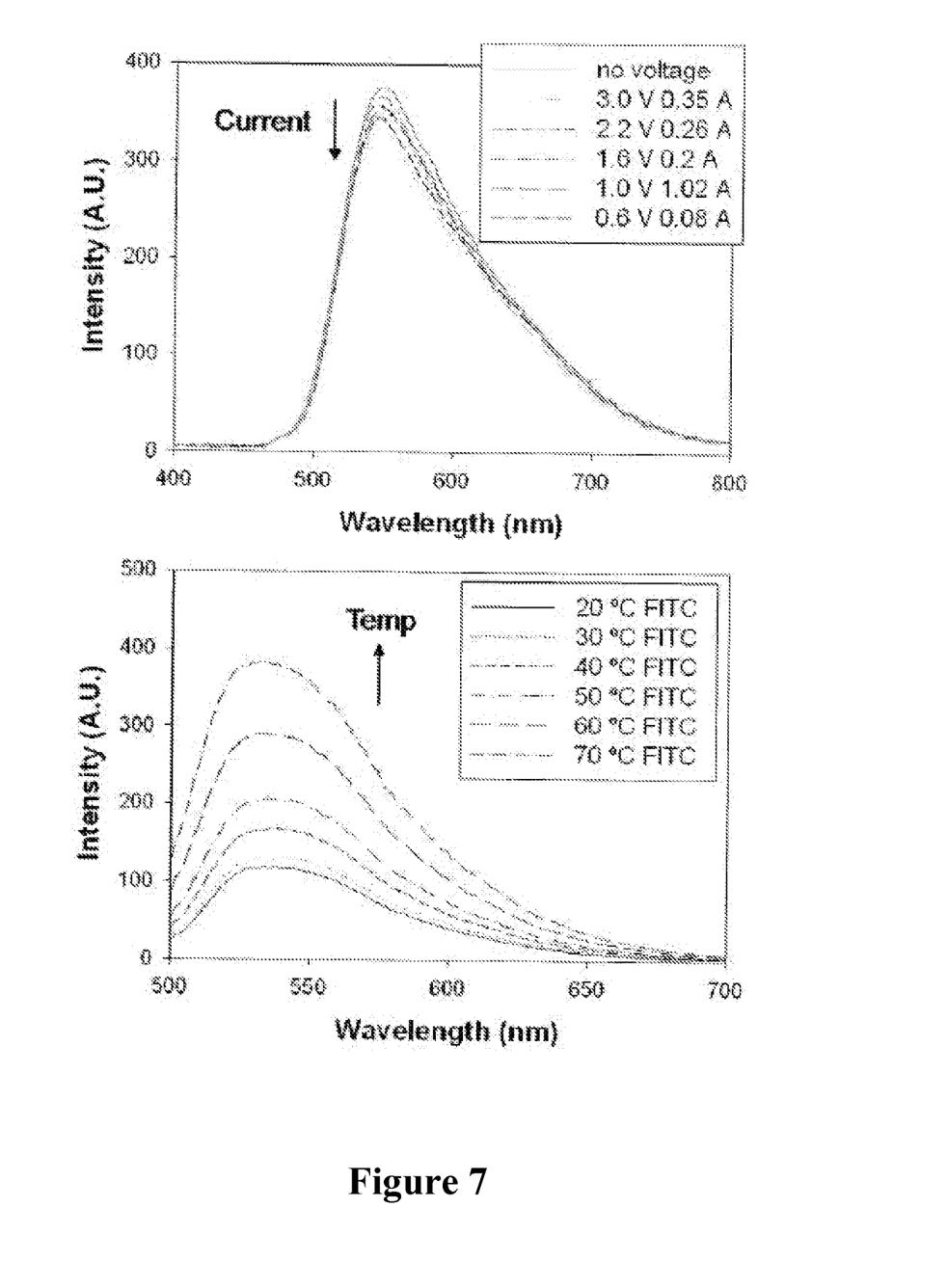
FIG. 7 shows the fluorescence spectra of FITC on almost-continuous SiFs (7Ω) with applied Voltage/Current gated "on" (Top). Fluorescence spectra of FITC in a cuvette as a function of temperature (Bottom).
Figure 8:
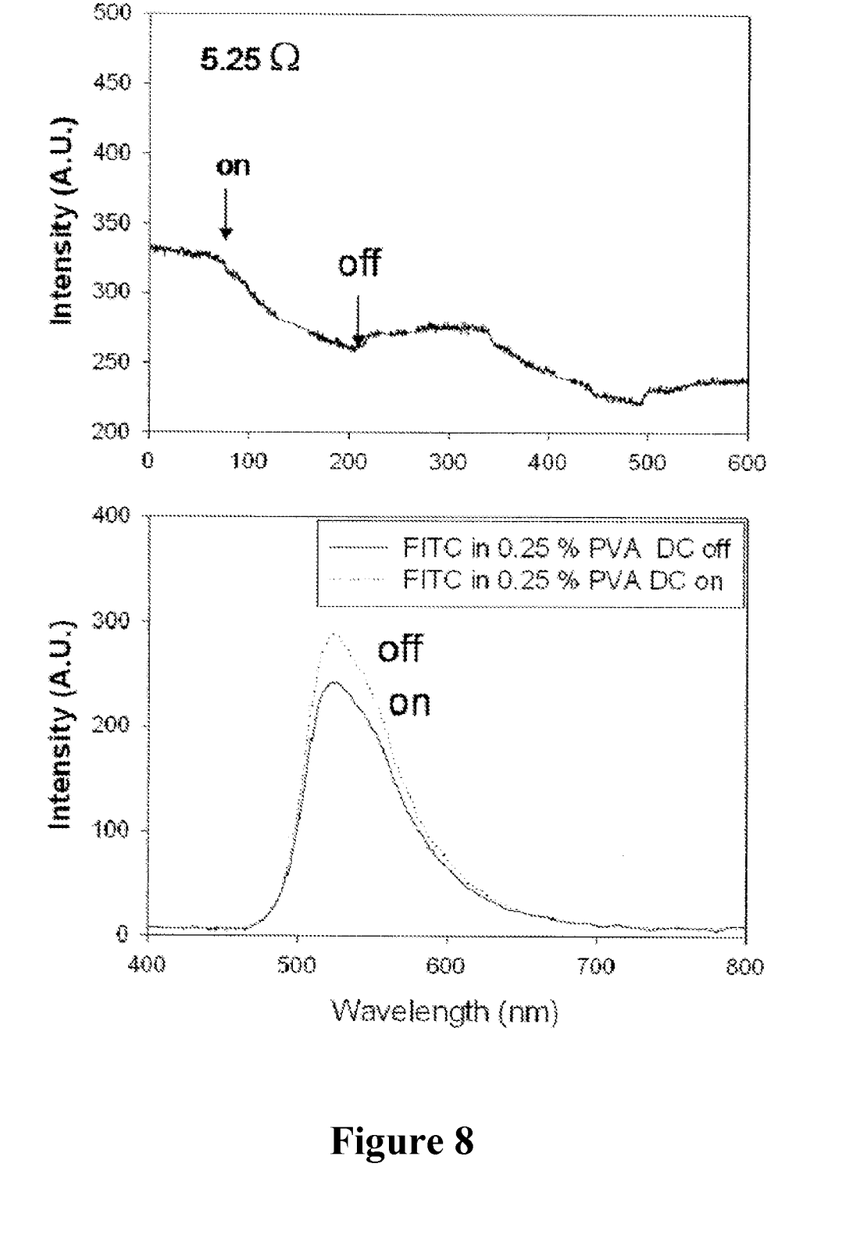
FIG. 8 shows Time dependent fluorescence emission (measured at 524 nm) of FITC doped in 0.25% PVA spin coated on semi-continuous SiFs with applied Voltage/Current gated "on" and "off" (Top). Fluorescence spectra of FITC on SiFs with applied Voltage/Current gated "on" and "off" (Bottom).

Surface oxidation and dipole re-orientation was also considered as a possible cause of the effect, as shown in FIG. 8. However, in a nitrogen purged thick 0.25% w/v PVA film ($\approx$37 nm), the fluorescence gating effect is still readily observed. It is interesting to consider the magnitude of the observed changes in fluorescence signal. From FIG. 1—Top, an $\approx$50% change was seen in the signal during current gating, however several factors are thought to account for the fluorescence signal not to change to an even further extent:

(1) FITC molecules are coated both on and between the silver islands, hence a large population are likely to be unaffected by an applied current;
(2) There is a slight temperature rise during gating which increases FITC emission, offsetting the magnitude of the observed effect. FIG. 7—Bottom shows FITC emission to increase as a function of temperature and thus can not account for the gating phenomenon. In this regard, the plasmon absorption of the SiFs is also shown to be unperturbed by an increased temperature, as shown in FIG. 6—Bottom); and
(3) The general decrease in fluorescence signal over time, both gated and not gated, is thought to be due to the photostability of FITC with constant CW 473 nm laser excitation.

Thus, depending on the excitable molecule, the change in the signal during current gating can be greater than 50% as found in FITC.

Figure 2:
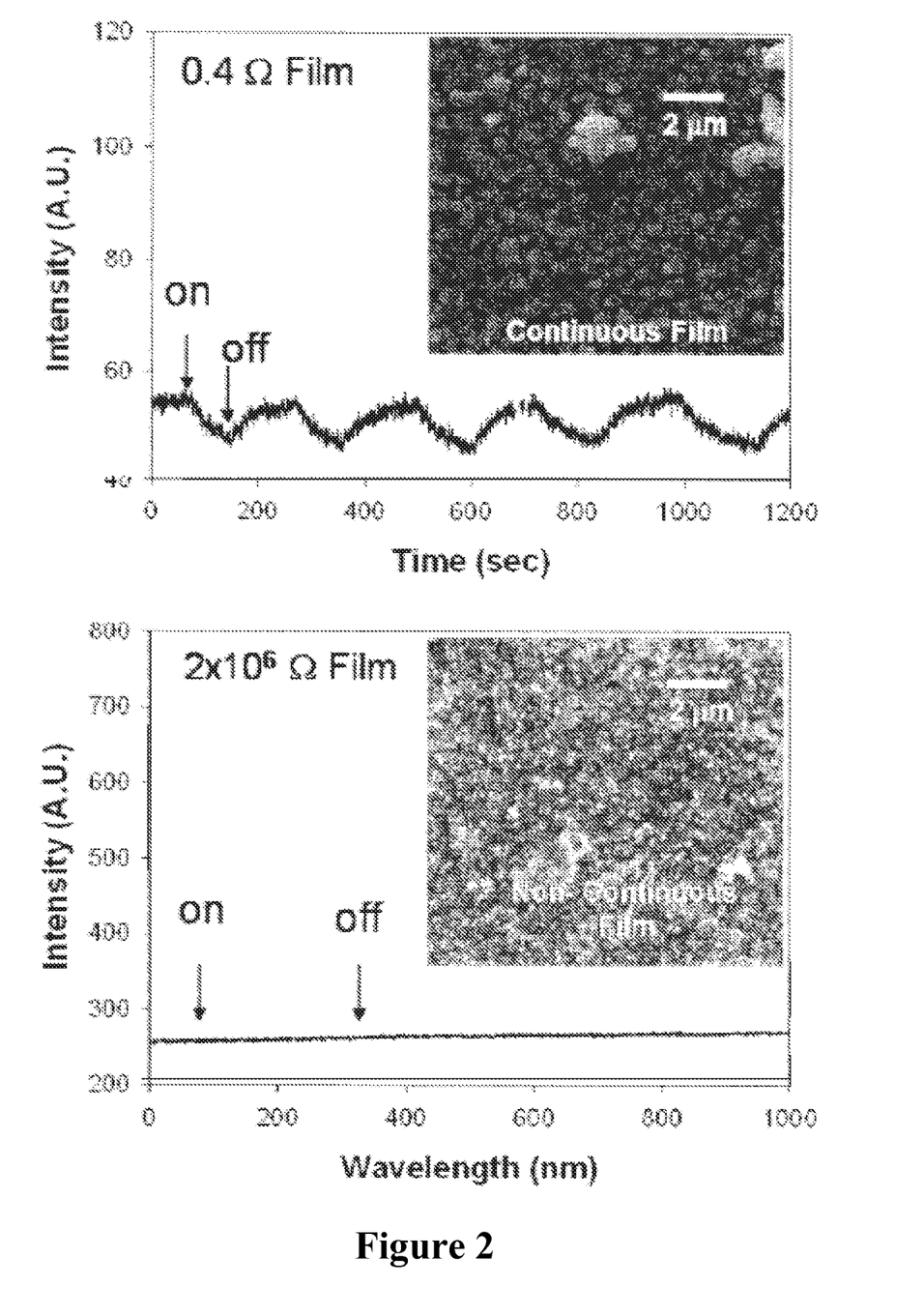
FIG. 2 shows the time-dependent fluorescence emission of FITC (measured at 544 nm), on (Top) almost continuous SiFs with applied voltage/current gated "on" and "off," and (Bottom) non-continuous SiFs with applied voltage/current gated "on" and "off" Inserts show the respective SEM images of the SiFs.
Figure 3:
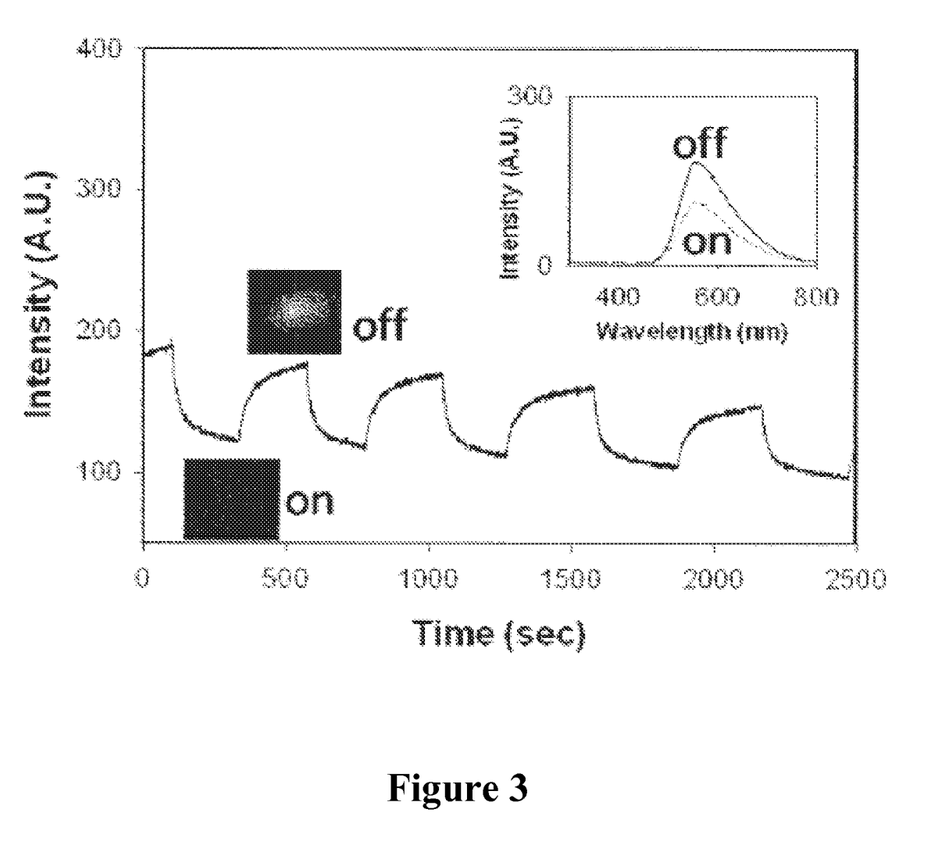
FIG. 3 shows the emissions of FITC with applied voltage/current gated "on" and "off" wherein the intensity of the emissions is detectably when the current is off

The effect of direct current on both very thick and thin films was studied, i.e. low and high resistance respectively, FIG. 2. Interestingly, for thicker films, the magnitude of the MEF effect is notably lower (55 a.u at time t=0) as compared to the low resistance films shown in FIG. 1, i.e. 190 a.u. This observation is completely consistent with the current understanding and interpretations of MEF,[1-4, 8] under the conditions employed here, continuous films can not support the generation of surface plasmons and therefore MEF. Non-continuous films, with a very high electrical resistance (i.e. low current flow), show a greater initial MEF effect, i.e. =260 a.u., FIG. 2—Bottom, consistent with other reports of MEF from SiFs.[1-4,8] Interestingly, both surfaces show a less pronounced fluorescence gating effect as the silver films shown in FIG. 1, indicating the effect is more pronounced for 'just continuous" films.

It is theorized that the possible mechanism which results in the observed effects as shown in FIGS. 1 and 2 includes that the plasmons in the just-continuous films shown in FIG. 1, which have a low electrical resistance, are not available for dipole coupling and MEF when a current is applied, and hence the MEF effect is gated. For thick films, FIG. 2—TOP, the films are sufficiently thick to allow current flow with the plasmons freely available for MEF, the net change in fluorescence observed being much smaller. For non-continuous films, which are ideal substrates for MEF, resistance to current flow is very high and hence no gating effect is observed, FIG. 2—Bottom. FIG. 4—Bottom outlines the proposed mechanism for the voltage/current gated MEF effect.

Finally, to place the results found in the present experiments in context with recent publications wherein a scanning tunneling microscope is used to excite localized plasmon resonances in metallic nanoparticles,[9,10] due to the local field of the tip. Iwasaki et al has subsequently shown that close-proximity luminophores to the nanoparticles are then subsequently excited resulting in molecular luminescence.[10] The system of the present invention is macroscopic in nature and indeed almost the inverse mechanism. After optical excitation and induced surface plasmons, an additional applied current across the nanoparticles film decreases the extent of fluorophore dipole coupling, reducing the overall MEF effect (FIG. 4—Bottom). Interestingly, while these other reports are single nanoparticle based and not nanoparticle films,[10] we have not been able to similarly observe fluorescence without the need for additional optical excitation. Similar to Iwasaki et al, the findings set forth herein are not dependent on the polarity, identical results obtained by simply switching around the electrical leads (data not shown).

From FIG. 1, an almost bi-exponential loss of fluorescence emission can be seen as the voltage is gated, eventually reaching a plateau over a few hundred seconds, i.e. <3 mins. Interestingly, at the onset of an applied current, the fluorescence intensity drops very rapidly indeed, within a few seconds. Later, the loss of emission is at a much slower rate. This rapid and then slow decay of fluorescence is thought to be underpinned by two competing processes. Initially, the fluorescence is off-gated by the passage of current, due to the inability of the surface plasmons to both dipole-couple and therefore enhances fluorescence, as discussed above. At later times, the silver island films were observed to have warmed slightly, which is shown in FIG. 7—Bottom, and this results in an increased fluorescein (FITC) fluorescence. Subsequently, a rapid off-gating effect, followed by slow surface heating, due to the resistance of the films to current flow, is thought to account for the bi-exponential loss of fluorescence observed in FIG. 1—Top.

While at first thought, surface heating appears to complicate the fluorescence gating observations, it is thought that the slight heating of surface samples could well facilitate the development of rapid assays, as has been recently reported by using focused low power microwaves and metallic nanoparticles.[11-13]

In conclusion, the first observation of gating MEF is shown in the present invention by the addition of an applied current across just-continuous silver films. The results suggest that for just-continuous films with an applied current, surface plasmons are not as readily available for near-field dipole coupling, the effect diminished as thicker metal is used, in essence increasing the number of charge carriers available for current flow and freeing up surface plasmons for dipole coupling.

REFERENCES

The contents of the references cited herein are incorporated by reference herein for all purposes.
(1) Geddes, C. D.; Lakowicz, J. R., Journal of *Fluorescence*, 2002, 121-129.
(2) Aslan, K.; Gryczynski, I.; Malicka, J.; Matveeva, E.; Lakowicz, J. R.; Geddes, C. D., *Current Opinion in Biotechnology* 2005, 16, 55-62.
(3) Zhang, Y.; Aslan, K.; Previte, M. J.; Geddes, C. D., *J Fluoresc* 2007, 17, 627-631.
(4) Aslan, K.; Geddes, C. D., *Analytical Chemistry* 2005, 77, 8057-8067.
(5) Aslan, K.; Malyn, S. N.; Geddes, C. D., *Analyst* 2007, 132, 1112-1121.
(6) Chowdhury, M. H.; Aslan, K.; Malyn, S. N.; Lakowicz, J. R.; Geddes, C. D., *Applied Physics Letters,* 2006, 88, 173 104.
(7) Boehm, D. A.; Gottlieb, P. A.; Hua, S. Z., *Sensors and Actuators B—Chemical* 2007, 126, 508-514.
(8) Aslan, K.; Zhang, Y.; Hibbs, S.; Baillie, L.; Previte, M. J.; Geddes, C. D., *Analyst* 2007, 132, 1130-8.
(9) Makinen, A. J.; Foos, E. E.; Wilkinson, J.; Long, J. P., *Journal of Physical Chemistry C,* 2007, 111, 8188-8194.
(10) Liu. H. W.; Ie, Y.; Nishitani R.; Aso, Y.; Iwasaki, H., *Physical Review B,* 2007, 75.
(11) Aslan, K.; Geddes, C. D., *Analytical Chemistry,* 2005, 77, 8057-8067.
(12) Aslan, K.; Geddes, C. D., *Plasmonics,* 2006, 1, 53-59.
(13) Aslan, K.; Geddes, C. D., *Anal Chem,* 2007, 79, 2131-6.

That which is claimed is:

1. A device system for use is an assay, the system comprising:
  a) a conductive metal surface on a substrate, wherein the conductive metal surface is a just continuous film having a resistance ranging from about 5 to 25 ohms, wherein the just-continuous film is a multiplicity of interconnected metallic particles selected from the group consisting of nanostructures, islands, colloids and a cracked surface with particle nature, and wherein the substrate includes glass, quartz, or a polymeric material;

b) a molecule positioned on or near the conductive metallic surface, wherein the molecule is a fluorophore, chromophore or luminophore and is capable of emitting electromagnetic energy upon excitation and wherein the fluorophore, chromophore or luminophore is positioned a distance from the conductive metallic surface to enhance the intensity of the emitting detectable electromagnetic energy and is positioned from about 10 to 20 nm from the metallic surface;

c) a source of electromagnetic energy with a wavelength sufficient to excite the fluorophore, chromophore or luminophore and cause the emission of electromagnetic energy;

d) a voltage source and an actuatable switch with the ability to be turned on and off and attached to the conductive metal surface of the interconnected metallic particles, wherein opening of the switch allows transference of direct current through the interconnected metallic particles which reduces or stops detectable electromagnetic energy emissions and closing of the switch provides for detectable electromagnetic energy emissions; and e) a detector for measuring emitting electromagnetic energy and/or a detector for measuring direct current through the conductive metal surface of the interconnected metallic particles.

2. The system of claim 1, wherein the conductive metal surface is fabricated from a metal selected from the group consisting of gold, silver, aluminum and copper.

3. The system of claim 1, wherein the voltage source is a battery, solar cell or hydrogen fuel cell.

4. The system of claim 1 wherein the system is used in a immunoassay, hybridization assay, resonance energy transfer assay, and polarization/anisotropy based assay, bioluminescence based assay, chemiluminescence based assay, luminescence based assay, or enzyme-linked immunosorbent assays.

5. The system of claim 1, wherein the exciting electromagnetic energy is in the range from UV to IRE.

* * * * *